United States Patent
Pfeiffer et al.

(10) Patent No.: US 7,871,792 B2
(45) Date of Patent: Jan. 18, 2011

(54) THERMACETOGENIUM PHAEUM CONSORTIUM FOR THE PRODUCTION OF MATERIALS WITH ENHANCED HYDROGEN CONTENT

(75) Inventors: Robert S. Pfeiffer, Parker, CO (US); Glenn A. Ulrich, Golden, CO (US); Gary Vanzin, Arvada, CO (US)

(73) Assignee: LUCA Technologies, Inc., Golden, CO (US)

( * ) Notice: Subject to any disclaimer, the term of this patent is extended or adjusted under 35 U.S.C. 154(b) by 392 days.

(21) Appl. No.: 12/127,076

(22) Filed: May 27, 2008

(65) Prior Publication Data

US 2008/0286855 A1    Nov. 20, 2008

Related U.S. Application Data

(62) Division of application No. 11/330,759, filed on Jan. 11, 2006, now Pat. No. 7,416,879.

(51) Int. Cl.
  C12P 39/00    (2006.01)
  C12P 3/00     (2006.01)
  C12P 5/02     (2006.01)
  C12N 1/20     (2006.01)

(52) U.S. Cl. .......... 435/42; 435/167; 435/168; 435/252.1; 435/252.4; 435/252.7; 435/281

(58) Field of Classification Search .......... None
See application file for complete search history.

(56) References Cited

U.S. PATENT DOCUMENTS

| | | |
|---|---|---|
| 1,990,523 A | 2/1935 | Buswell et al. |
| 2,413,278 A | 12/1946 | Zobell |
| 2,641,566 A | 6/1953 | Zobell |
| 2,659,659 A | 11/1953 | Schmidl |
| 2,660,550 A | 11/1953 | Updegraff et al. |
| 2,807,570 A | 9/1957 | Updegraff |
| 2,907,389 A | 10/1959 | Hitzman |
| 2,975,835 A | 3/1961 | Bond |
| 3,006,755 A | 10/1961 | Adams |
| 3,185,216 A | 5/1965 | Hitzman |
| 3,332,487 A | 7/1967 | Jones |
| 3,340,930 A | 9/1967 | Hitzman |
| 3,437,654 A | 4/1969 | Dix |
| 3,637,686 A | 1/1972 | Kokubo et al. |
| 3,640,846 A | 2/1972 | Johnson |
| 3,724,542 A | 4/1973 | Hamilton |
| 3,800,872 A | 4/1974 | Friedman |
| 3,826,308 A | 7/1974 | Compere-Whitney |
| 3,982,995 A | 9/1976 | Yen et al. |
| 4,184,547 A | 1/1980 | Klass et al. |
| 4,300,632 A | 11/1981 | Wilberger et al. |
| 4,316,961 A | 2/1982 | Klass et al. |
| 4,329,428 A | 5/1982 | Ghosh et al. |
| 4,349,633 A | 9/1982 | Worne et al. |
| 4,358,535 A | 11/1982 | Falkow et al. |
| 4,358,537 A | 11/1982 | Chynoweth |
| 4,386,159 A | 5/1983 | Kanai |
| RE31,347 E | 8/1983 | Reijonen et al. |
| 4,416,332 A | 11/1983 | Wiberger et al. |
| 4,424,064 A | 1/1984 | Klass et al. |
| 4,446,919 A | 5/1984 | Hitzman |
| 4,450,908 A | 5/1984 | Hitzman |
| 4,475,590 A | 10/1984 | Brown |
| 4,481,293 A | 11/1984 | Thomsen et al. |
| 4,522,261 A | 6/1985 | McInerney et al. |
| 4,562,156 A | 12/1985 | Isbister et al. |
| 4,579,562 A | 4/1986 | Tarman et al. |
| 4,610,302 A | 9/1986 | Clark |
| 4,640,767 A | 2/1987 | Zajic et al. |
| 4,666,605 A | 5/1987 | Minami et al. |
| 4,678,033 A | 7/1987 | Killough |
| 4,799,545 A | 1/1989 | Silver et al. |
| 4,826,769 A | 5/1989 | Menger |
| 4,845,034 A | 7/1989 | Menger et al. |
| 4,883,753 A | 11/1989 | Belaich et al. |

(Continued)

FOREIGN PATENT DOCUMENTS

DE    4036787 B1    5/1992

(Continued)

OTHER PUBLICATIONS

Johnson et al., 1991, "Preliminary Results of a Coalbed Methane Assessment of the Wind River Indian Reservation, Whoming" Coalbed Methane, pp. 273-284.

(Continued)

*Primary Examiner*—Herbert J Lilling
(74) *Attorney, Agent, or Firm*—Townsend and Townsend and Crew LLP (57) ABSTRACT

An isolated microbial consortium is described that includes a first microbial consortium having *Thermacetogenium phaeum* to metabolize a complex hydrocarbon substrate into metabolic products comprising an acetate compound. The consortium also includes a second microbial consortium having a methanogen to convert the acetate compound into a final product that includes methane. Also, a method of increasing production of materials with enhanced hydrogen content. The method includes isolating *Thermacetogenium phaeum* from geologic formation water, culturing the isolated *Thermacetogenium phaeum* to increase the *Thermacetogenium phaeum* population, and introducing a consortium of the cultured *Thermacetogenium phaeum*, which may include spores of *Thermacetogenium phaeum*, into a hydrocarbon formation containing a complex hydrocarbon substrate.

14 Claims, 8 Drawing Sheets

U.S. PATENT DOCUMENTS

| | | | |
|---|---|---|---|
| 4,905,761 A | 3/1990 | Bryant | |
| 4,906,575 A | 3/1990 | Silver et al. | |
| 4,914,024 A | 4/1990 | Strandberg et al. | |
| 4,947,932 A | 8/1990 | Silver et al. | |
| 4,971,151 A | 11/1990 | Sheehy | |
| 5,044,435 A | 9/1991 | Sperl et al. | |
| 5,076,927 A | 12/1991 | Hunter | |
| 5,083,610 A | 1/1992 | Sheehy | |
| 5,083,611 A | 1/1992 | Clark et al. | |
| 5,087,558 A | 2/1992 | Webster, Jr. | |
| 5,100,553 A | 3/1992 | Nomura et al. | |
| 5,155,042 A | 10/1992 | Lupton et al. | |
| 5,163,510 A | 11/1992 | Sunde | |
| 5,297,625 A | 3/1994 | Premuzic et al. | |
| 5,327,967 A | 7/1994 | Jenneman et al. | |
| 5,340,376 A | 8/1994 | Cunningham | |
| 5,341,875 A | 8/1994 | Jenneman et al. | |
| 5,350,684 A | 9/1994 | Nakatsugawa et al. | |
| 5,360,064 A | 11/1994 | Jenneman et al. | |
| 5,363,913 A | 11/1994 | Jenneman et al. | |
| 5,368,099 A | 11/1994 | Davey et al. | |
| 5,424,195 A | 6/1995 | Volkwein | |
| 5,492,828 A | 2/1996 | Premuzic et al. | |
| 5,500,123 A | 3/1996 | Srivastava | |
| 5,510,033 A | 4/1996 | Ensley et al. | |
| 5,516,971 A | 5/1996 | Hurley | |
| 5,538,530 A | 7/1996 | Heaton et al. | |
| 5,551,515 A | 9/1996 | Fodge et al. | |
| 5,560,737 A | 10/1996 | Schuring et al. | |
| 5,593,886 A | 1/1997 | Gaddy | |
| 5,597,730 A | 1/1997 | Aust et al. | |
| 5,630,942 A | 5/1997 | Steiner | |
| 5,670,345 A | 9/1997 | Srivastava et al. | |
| 5,695,641 A | 12/1997 | Cosulich et al. | |
| 5,723,597 A | 3/1998 | Kohne | |
| 5,763,736 A | 6/1998 | Daume | |
| 5,854,032 A | 12/1998 | Srivastava et al. | |
| 5,858,766 A | 1/1999 | Premuzic et al. | |
| 5,885,825 A | 3/1999 | Lin et al. | |
| 5,919,696 A | 7/1999 | Ikeda et al. | |
| 5,928,864 A | 7/1999 | Kohne | |
| 5,955,261 A | 9/1999 | Kohne | |
| 5,955,262 A | 9/1999 | Kourilsky et al. | |
| 6,090,593 A | 7/2000 | Fleming et al. | |
| 6,143,534 A | 11/2000 | Menger et al. | |
| 6,202,051 B1 | 3/2001 | Woolston | |
| 6,210,955 B1 | 4/2001 | Hayes | |
| 6,265,205 B1 | 7/2001 | Hitchens et al. | |
| 6,543,535 B2 | 4/2003 | Converse et al. | |
| 6,758,270 B1 | 7/2004 | Sunde et al. | |
| 6,795,922 B2 | 9/2004 | Johnson et al. | |
| 6,859,880 B2 | 2/2005 | Johnson et al. | |
| 7,416,879 B2 | 8/2008 | Pfeiffer et al. | |
| 2001/0045279 A1 | 11/2001 | Converse et al. | |
| 2003/0062270 A1 | 4/2003 | McAlister | |
| 2003/0205458 A1 | 11/2003 | Roychowdhury | |
| 2003/0216353 A1 | 11/2003 | Mosher et al. | |
| 2004/0033557 A1 | 2/2004 | Scott et al. | |
| 2004/0035785 A1 | 2/2004 | Rebholz | |
| 2004/0228833 A1 | 11/2004 | Costantino et al. | |
| 2005/0053955 A1 | 3/2005 | Sowlay et al. | |
| 2005/0269261 A1 | 12/2005 | Sublette | |
| 2006/0223153 A1 | 10/2006 | Pfeiffer et al. | |
| 2006/0223159 A1 | 10/2006 | Pfeiffer et al. | |
| 2006/0223160 A1 | 10/2006 | Vanzin | |
| 2008/0182318 A1 | 7/2008 | Vanzin | |
| 2009/0035840 A1 | 2/2009 | Pfeiffer et al. | |
| 2010/0035309 A1 | 2/2010 | Havemen et al. | |

FOREIGN PATENT DOCUMENTS

| | | |
|---|---|---|
| DE | 4115435 B2 | 8/1992 |
| DE | 19520548 B3 | 12/1996 |
| JP | 09 121868 B4 | 5/1997 |
| WO | WO 79/00201 B5 | 4/1979 |
| WO | WO 89/10463 A1 | 11/1989 |
| WO | WO 92/13172 A1 | 8/1992 |
| WO | WO 01/68904 B6 | 9/2001 |
| WO | WO 02/34931 A2 | 5/2002 |
| WO | WO 2005/005773 | 1/2005 |
| WO | WO 2006/108136 A | 10/2006 |

OTHER PUBLICATIONS

Luo Hong-Wei et al: "Differential expression of methanogenesis genes of *Methanothermobacter thermoautotrophicus*(former *Methanobacterium thermoautotrophicum*) in pure culture and in cocultures with fatty acid-oxidizing synthrophs": Applied and Environmental Microbiology, vol. 68, No. 3, Mar. 2002, pp. 1173-1179, XPOO2551248 ISSN: 0099-2240.

Abbanet et al., "Microbiology and biochemistry of the methanogenic archaeobacteria", Adv. Space Res., vol. 9(6):101-105, 1989.

Beller, Harry R. et al., "A Real-Time Polymerase Chain Reaction Method for Monitoring Anaerobic, Hydrocarbon-Degrading Bacteria Based on a Catalog Gene," Environ. Sci. Technol. 2002, vol. 36, No. 18, pp. 3977-3984.

Grundmann, Olav et al., "Genes Encoding the Candidate Enzyme for Anaerobic Activation of n-alkanes in the Dentrifying Bacterium, Strain HxN1," Journal compilation © 2007 Society for Applied Microbiology and Blackwell Publishing Ltd., pp. 1-10.

Harrison, Faith H. et al., "The *pim*FABCDE Operon from *Rhodopseudomonas palustris* Mediates Dicarboxylic Acid Degradation and Participates in Anaerobic Benzoate Degradation," Microbiology (2005), 151, pp. 727-736.

Hedderich, Reiner et al., "Physiology and Biochemistry of the Methane-Producing Archaea," Prokaryotes (2006), Chapter 1.34, pp. 1050-1079.

Heider, Johann, "Adding Handles to Unhandy Substrates: Anaerobic Hydrocarbon Activation Mechanisms," Current Opinion in Chemical Biology, 2007, 11:188-194, www.sciencedirect.com.

Kuntze, Kevin et al., "6-Oxocyclohex-1-ene-carbonyl-coenzyme A hydrolases from obligately anaerobic bacteria: characterization and identification of its gene as a functional marker for aromatic compounds degrading anaerobes," Journal compilation © 2008 Society for Applied Microbiology and Blackwell Publishing Ltd. pp. 1-10.

Leaphart, Adam B. et al., "Recovery and Analysis of Formyltetrahydrofolate Synthetase Gene Sequences from Natural Populations of Acetogenic Bacteria," Applied and Environmental Microbiology, Mar. 2001, vol. 67, No. 3, pp. 1392-1395.

Peters, Franziska et al., "Genes, Enzymes, and Regulation of *para*-Cresol Metabolism in *Geobacter metallireducens*," Journal of Bacteriology, Jul. 2007, pp. 4729-4738.

Vignais, Paulette M. et al., "Occurrence, Classification, and Biological Function of Hydrogenases: An Overview," Chem. Rev. 2007, pp. 4206-4272.

Wagner, Michael et al., "Functional Marker Genes for Identification of Sulfate-Reducing Prokaryotes," Methods in Enzymology, vol. 397, Copyright 2005, Elsevier Inc., pp. 469-489.

Wilkes, Heinz et al., "Anaerobic Degradation of *n*-hexane in a Dentrifying Bacterium: Further Degradation of the Initial Intermediate (1-methylpentyl) succinate via C-skeleton Rearrangement," Arch Microbiol (2002), pp. 235-242.

Wofford, Neil Q. et al., "Preparation of Cell-Free Extracts and the Enzymes Involved in Fatty Acid Metabolism in *Syntrophomonas wolfei*," Journal of Bacteriology, Jul. 1986, p. 179-185.

Freedman et al., "Biodegradation of Chloromethane by *Pseudomonas aeruginosa* Strain NB1 Under Nitrate-Reducing and Aerobic Conditions", Applied and Environmental Microbiology, Aug. 2004, vol. 70, No. 8, pp. 4629-4634, especially abstract, p. 4629, col. 2.

Miralles et al., "Effects of Spilled Oil on Bacterial Communities of Mediterranean Coastal Anoxic Sediments Chronically Subjected to Oil Hydrocarbon Contamination", Microbial Ecology, Mar. 2004, vol. 54, pp. 646-661, especially p. 654 col. 2-p. 655 col. 1; p. 656, fig. 7.

Aitken, Carolyn M. et al "Anaerobic hydrocarbon degradation in deep subsurface oil reserves" Nature, Sep. 16, 2004, pp. 291-294.

Anderson, Robert T., and Lovley, Derek R., "Hexadecane Decay by Methanogenesis", Nature, v. 404, p. 722, Apr. 13, 2000.

Anderson, Robert T., Rooney-Varga, Juliette N., et al., "Anaerobic Benzene Oxidation in the Fe(III) Reduction Zone of Petroleum-Contaminated Aquifers", Environmental Science & Technology, v. 32, pp. 1222-1229, 1998.

Artech Inc., Biological Gasification of Coals. Final Report, U.S. Department of Energy, Contract DE-AC21-87MC23285, pp. 40-63, 1990.

Basiliko, Nathan et al. "Influence of Ni, Co, Fe, and Na additions on methane production in *Sphagnum* dominated Northern American peatlands" Biogeochemistry, 2001, 52: 133-153.

Belyaev, S. S., et al. "Methanogenic Bacteria from the Bondyuzhskoe Oil Field: General Characterization and Analysis of Stable-Carbon Isotopic Fractionation" Applied and Environmental Microbiology, 1983, v. 45, No. 2, pp. 691-697.

Bernard, F. P., et al. "Indigenous Microorganisms in Connate Water of Many Oil Fields: A New Tool in Exploration and Production Techniques" SPE 24811, 1992, pp. 467-476.

Boone, David R. et al.—"Bergey's Manual of Systematic Bacteriology—Second Edition- vol. One " The Archaea and the Deeply Branching and Phototropic Bacteria, Springer, 4 pages, Pub date 1985.

Boopathy, R., "Anaerobic degradation of No. 2 diesel fuel in the wetland sediments od Barataria-Terrebone estuary under various electron acceptor conditions," Bioresource Technology 2003, vol. 86, pp. 171-175.

Brockman, Fred "Regulation of Microbial Communities" at http://www.sysbio.org/sysbio/microbial/index.stm, 2005, 2 pages.

Brown, L.R., and Vadie, A.A., "Slowing Production Decline and Extending the Economic Life of an Oil Field: New MEOR Technology", SPE 59306; SPE/DOE Improved Oil Recovery Symposium, Tulsa, Oklahoma, Apr. 3-5, 2000.

Budwill, Karen "Microbial Methanogenesis and its Role in Enhancing Coalbed Methane Recovery" (Canadian Coals) CSEG Recorder (Nov. 2003) pp. 41-43.

Cervantes, Francisco J. et al, "Competition between methanogenesis and quinone respiration for ecologically important substrates in anaerobic consortia" FEMS Microbiology Ecology 34, 2000, pp. 161-171.

Claypool, George E. et al. "The Origin and Distribution of Methane in Marine Sediments" *Natural Gases in Marine Sediments*, Ed. Isaac R. Kaplan, 1974, pp. 99-139.

Claypool, George E. "Geochemical Characterization of Biogenic Gas and Coalbed Methane in Shallow Gas Fields: Eastern Denver Basin, Powder River Basin and Williston Basin" Luca Technologies, Inc. Internal Report, Jul. 8, 2001, 29 pages.

Clayton et al., "Oil-Generating Coals of the San Juan Basin, New Mexico and Colorado, U.S." Org. Geochem. 1991, pp. 735-742, vol. 17, No. 6.

Clayton, C. et al. "Source Volumetrics of Biogenic Gas Generation" Bacterial Gas, Ed. R. Vially, 1992, pp. 191-204, Paris.

Coates, John D., Anderson, Robert T., et al., "Anaerobic Hydrocarbon Degradation in Petroleum-Contaminated Harbor Sediments under Sulfate-Reducing and Artificially Imposed Conditions", Environ. Sci. Technol., vol. 30, No. 9, pp. 2784-2789, 1996.

Connan, J. et al. Anaerobic biodegradation of petroleum in reservoirs: a widespread phenomenon in nature: 18th International Meeting on Organic Geochemistry Sep. 22-26, 1997 Maastricht, The Netherlands (Abstr.), p. O2: 5-6.

Connan, J. et al. "Origin of Gases in Reservoirs" 1995 International Gas Research Conference, 1996, pp. 21-41.

Conrad, R. "Contribution of hydrogen to methane production and control of hydrogen concentrations in methanogenic soils and sediments" FEMS Microbiology Ecology, 28 (1999) pp. 193-202.

DeBruin, R.H. et al. "Coalbed Methane In Wyoming" Wyoming State Geological Survey (Laramie, WY), Information Pamphlet 7 (second revision), 2004, 24 pages.

Donaldson et al., "Conference Focuses on Microbial Enhancement of Oil Recovery," The Oil and Gas Journal, pp. 47-52, Dec. 20, 1982.

Donaldson, Eric C. et al. Microbial Enhanced Oil Recovery, Developments in Petroleum Science, 1989, v. 22, pp. 1-14, 121, 123, 149, Elsevier.

Faber, E. et al. "Distinction of Bacterial and Thermogenic Hydrocarbon Gases" Bacterial Gas, Ed. R. Vially, 1992, pp. 63-74, Paris.

Ficker et al., "Molecular Characterization of a Toluene-Degrading Methanogenic Consortium," Applied and Enviromental Microbiology, Dec. 1999, vol. 65, pp. 5576-5585.

Flesner, R. et al. "Pilot-scale base hydrolysis processing of HMX-based plastic-bonded explosives", 4th International Symposium on Special Topics in Chemical Propulsion: Challenges In Propellants and 100 Years After Nobel, May 27-31, 1996, pp. 213-220.

Flesner, R. et al., "Pilot-scale base hydrolysis processing of HMX-based plastic-bonded explosives", Chemical Abstracts, vol. 130, No. 5, Feb. 1, 1998, Columbus, Ohio, U.S.; Abstract No. 54464a, pp. 835.

Gaasterland, Terry "Archaeal Genomics" Current Opinions in Microbiology (1999) 2:542-547.

Galagan, James. E. et al., "The Genome of M. *acetivorans* Reveals Extensive Metabolic and Physiological Diversity" Genome Research 12: 532-542 (2002).

Gilles Ravot et al., "Fusibacter Paucivorans Gen. Nov., Sp. Nov., an Anaerobic, Thiosulfate-Reducing Bacterium From an Oil-Producing Well," International Journal of Systematic Bacteriology (1999) 49, 1141-1147.

Grbic-Galic, D., and Vogel, T. "Transformation of Toluene and Benzene by mixed methanogenic cultures" Applied and Environmental Microbiology, 1987, v. 53, pp. 254-260.

Groudeva, V. I. et al. "Enhanced Oil Recovery by Stimulating the Activity of the Indigenous Microflora of Oil Reservoirs": Biohydrometallurgical Technologies (Eds. Torma, A. E., Apel, M.L.; and Brierlay, C.L.): Minerals, Metals, & Mater. Soc. Biohydromet. Technol. Int. Symp, 1993 (Jackson Hole, Wy. 93.8.22-25) Proc., v. 2, pp. 349-356.

Gullapalli, Irene L. et al., "Laboratory Design and Field Implementation of Microbial Profile Modification Process", SPE Reservoir Evaluation & Engineering, v. 3, No. 1, pp. 42-49, Feb. 2000.

Halbouty, M.T. "East Texas Field—USA, East Texas Basin, Texas; in Stratigraphic Traps II" (compiled by N.H. Foster, and E.A. Beaumont) AAPG Treatise of Petroleum Geology, Atlas of Oil and Gas Fields, 1991, pp. 189-206.

Hales, B.A. et al, "Isolation and Identification of Methanogen-specific DNA from Blanket Bog Peat by PCR Amplification and Sequence Analysis", Applied and Environmental Microbiology, 1996, pp. 668-675.

Hattori, Satoshi et al.; "Thermacetogenium phaeum gen.nov.,sp.nov., a strictly anaerobic, thermophilic, syntrophic acetate-oxidizing bacterium", Internation. Journal of Systematic and Evolutionary Microbiology (2000), 50, 1601-1609, 9 pages, 2000.

Hermann, M. et al. "Anaerobic Microflora of Oil Reservoirs: Microbiological Characterization of Samples from Some Production Wells" Bacterial Gas (R. Vially Ed.) Editions Technip. Paris, 1992, pp. 223-233.

Hunkeler et al., "Petroleum Hydrocarbon Mineralization in Anaerobic Laboratory Aquifer Columns," Journal of Contaminant Hydrology 32, pp. 41-61, 1998.

Ivanov, M. V. et al. "Additional Oil Production During Field Trials in Russia: Microbial Enhancement of Oil Recovery—Recent Advances" (4th US DOE MEOR Int Conf (Upton, NY, 1992) Proc; Elsevier Develop Petrol Sci Ser No. 39), 1993, pp. 373-381.

Ivanov, M. V. et al. "Die mikrobiologische Bildung von Methan in einer abzubauenden Erdöllagerstätte" Frieberger Forschungshefte Reihe C, v., 1982, vol. 389, pp. 189-199.

Johnson, Ronald C. et al., "A Preliminary Evaluation of Coalbed Methane Resources of the Wind River Indian Reservation, Wyoming" Coal-Bed Methane Potential of the Wind River Indian Reservation, Ed. Stephen Manydeeds, Dec. 1991, pp. 40-64, Bureau of Indian Affairs Division of Energy and Mineral Resources.

Kasting, James F. "When Methane Made Climate" Scientific American, Jul. 2004, pp. 80-85.
Kazuya Wantabe et al., "Diversity and Abundance of Bacteria in An Underground Oil-Storage Cavity," BMC Microbiology, pp. 1-10, Publ Date Aug. 28, 2002.
Kim, Ann G. "Experimental Studies on the Origin and Accumulation of Coalbed Gas" U.S. Dept. of the Interior Bureau of Mines, Report of Investigations 8317, 1978, 18 pages.
Kim, Ann G. et al. "Hydrocarbon Gases Produced in a Simulated Swamp Environment" U.S. Dept. of the Interior Bureau of Mines, Report of Investigations 7690, 1972, 13 pages.
Klein, A. et al. "Comparative Analysis of Genes Encoding Methyl Coenzyme M Reductase in Methanogenic Bacteria", Mol Gen Genet, 1988, 213:409-420.
Krumholtz, Lee R. et al. "Confined subsurface microbial communities in Cretaceous Rock" Nature (Mar. 6, 1997) pp. 64-66.
Kunzig, Robert "20,000 Microbes Under the Sea" Mar. 2004, pp. 32-41, vol. 25, No. 3.
Law, Ben E. et al "Coalbed Gas Accumulations in the Paleocene Fort Union Formation, Powder River Basin, Wyoming" Coalbed Methane—1991; Rocky Mountain Association of Geologists, pp. 179-190.
Le Blanc, Leonard, Artificial Recharge, Offshore, p. 10, Feb. 2000.
L'Haridon, S., Reysenbach, A.L., et al., Hot Subterranean Biosphere in a Continental Oil Reservoir, Nature, v. 377, pp. 223-224, Sep. 21, 1995.
Li, M. et al. "Advances in Simulated Tests of Biogas" Oil & Gas Geology, 1996, v. vol. 17, No. 2, pp. 117-122, with abstract.
Lollar, B. Sherwood et al. "Evidence for bacterially generated hydrocarbon gas in Canadian Shield and Fennoscandian Shield rocks" Geochemicaet Cosmochimica Acta vol. 57, pp. 5073-5085 (1993).
Lomans, Bart P. et al. "Isolation and Characterization of *Mehanomethylovorans hollandica* gen. nov., sp. nov., Isolated from Freshwater Sediment, a Methyltrophic Methanogen Able to Grow on Dimethyl Sulfide and Methanethiol." Applied and Env. Microbiology, Aug. 1999, p. 3641-3650, vol. 65.
Lovely, Derek R. "Deep Subsurface Microbial Processes" Reviews of Geophysics, 33, Aug. 3, 1995, pp. 365-381.
Magot, Michel et al. "Microbiology of Petroleum Reservoirs" Antonie van Leeuwenhoek, 2000, 77: 103-116.
Mattavelli, L. et al. "Deep Isotopic Light Methane in Northern Italy" Bacterial Gas, Ed. R. Vially, 1992, pp. 121-132.
McDonald, I.R. et al. "Molecular Ecological Analysis of Methanogens and Methanotrophs in Blanket Bog Peat" Microbial Ecology (1999) 38:225-233.
Middledorp et al., "Enrichment and Properties of a 1,2,4-trichlorobenzene-Dechlorinating Methanogenic Microbial Consortium," Applied and Environmental Microbiology, Apr. 1997, vol. 63, pp. 1225-1229.
Nandi, R et al. "Microbial Production of Hydrogen: An Overview" Critical Reviews in Microbiology, 24 (1): 61-84 (1998).
Nazina, T. N. et al. "Occurrence and Geochemical Activity of Microorganisms in High-Temperature, Water-Flooded Oil Fields of Kazakhstan and Western Siberia" Geomicrobiology Journal, 1995, v. 13, pp. 181-192.
Nazina, T. N. et al. "Microbial Oil Transformation Processes Accompanied by Methane and Hydrogen-Sulfide Formation" Geomicrobiology Journal, 1985, vol. 4, No. 2, pp. 103-130.
Neue, Heinz-Ulrich "Methan Emission from Rice Fields", BioScience, 1993, pp. 466-473, vol. 43, No. 7, downloaded from http://www.ciesin.org/docs/004-032/004-032.html.
Ng, T. K., and Weimer, P. J., "Possible Nonanthropogenic Origin of Two Methanogenic Isolates from Oil-Producing Wells in the San Miguelito Field, Ventura County, California", Geomicrobiology Journal, 1989, v. 7, pp. 185-192.
O'Carroll, Christopher "The Pervasive Presence of Microbes" http://www/umassmag.com/Summer_2003/The_pervasive_presence_of_microbes_5_08.htm, 2003, 3 pages.
Ooteghem et al., "Hydrogen Production by the Thermophilic Bacterium, Thermotogo Neapolitana," Proceedings of the 2001 DOE Hydrogen Program Review, 2001, pp. 1-12.

Orphan et al., "Culture-Dependant and Culture-Independent Characterization of Microbial Assemblages Associated with High-Temperature Petroleum Reservoirs," American Society for Microbiology, pp. 700-711, 2000.
Panow, A. et al. "Mechanisms of Biologically-Mediated Methane Evolution from Black Coal", Fuel Processing Technology v. 52, pp. 115-125, 1997.
Pedersen, K. "Exploration of Deep Intraterrestrial Microbial Life: Current Perspectives" FEMS Microbiology Letters 185 (2000) pp. 9-16.
Potter et al. "Artificial Recharge," Offshore, Feb. 2000, pp. 10.
Puri et al. "Enhanced Coalbed Methane Recovery" Proceedings 1990 SPE Annual Technical Conference and Exhibition Reservoir Engineering, Sep. 23-26, 1990, New Orleans, Louisiana, SPE 20732, 1990, pp. 193-202.
Rahman et al., "Towards efficient Crude Oil Degradation by a mixed bacterial consortium," Bioresource Technology, 2002, vol. 85, pp. 257-261.
Reeve, John N. "Archaebacteria Then . . . Archaes Now (Are There Really No Archaeal Pathogens?)" Journal of Bacteriology, vol. 181, No. 12, Jun. 1999 pp. 3613-3617.
Revesz, K. et al. "Methane production and consumption monitored by stable H and C isotope ratios at a crude oil spill site, Bemidji, Minnesota" Applied Geochemistry, 1995, vol. 10, pp. 505-515.
Rice, Dudley D. "Controls, habitat, and resource potential of ancient bacterial gas", Bacterial Gas, Ed. Vially, R., 1992, pp. 91-118, Paris.
Rice, Dudley D. et al. "Characterization of coal-derived hydrocarbons and source-rock potential of coal beds, San Juan Basin, New Mexico and Colorado, U.S.A." International Journal of Coal. Geology, 1989, pp. 597-626, vol. 13.
Rice, Dudley D. et al. "Composition and Origins of Coalbed Gas" Hydrocarbons from Coal: American Association of Petroleum Geologists Studies in Geology #38, Eds. Law, B.E., and Rice, D.D., 1993, pp. 159-184.
Rice, Dudley D. et al. "Generation, Accumulation, and Resource Potential of Biogenic Gas" The American Association of Petroleum Geologists Bulletin, vol. 65, No. 1, Jan. 1981.
Rice, Dudley D. et al. "Identification and Significance of Coal-Bed Gas, San Juan Basin, Northwestern New Mexico and Southwestern Colorado" *Geology and Coal-Bed Methane Resources of the Northern San Juan Basin*, Colorado and New Mexico, Ed. J. Fassett, Coal-Bed Methane, San Juan Basin, 1988, pp. 51-59, Rocky Mountain Association of Geologists.
Rice, Dudley D. et al. "Nonassociated Gas Potential of San Juan Basin Considerable" Oil & Gas Journal, Aug. 1990, pp. 60-61, vol. 88, No. 33.
Ridgley, J.L. et al. "Re-Evaluation of the Shallow Biogenic Gas Accumulation, Northern Great Plains, USA—Is the Similar Gas Accumulation in Southeastern Alberta and Southwestern Saskatchewan a Good Analog?" Summary of Investigations (1999) vol. 1 pp. 64-78.
Rightmire, C.T. et al. "Coalbed Methane Resource", 1984, Coalbed methane resources of the United States, AAPG Studies in Geology #17, Tulsa, p. 1-B.
Rooney-Varga, Juliette N. et al. "Microbial Communities Associated with Anaerobic Benzene Degradation in a Petroleum-Contaminated Aquifer", Applied and Environmental Microbiology, v. 65, No. 7, pp. 3056-3063, Jul. 1999.
Rozanova, E.P. et al. "Distribution of Sulfate-Reducing Bacteria Utilizing Lactate and Fatty Acids in Anaerobic Ecotopes of Flooded Petroleum Reservoirs" Institute of Microbiology, Academy of Sciences of the USSR, Moscow. Translated from Mikrobiologiya, vol. 60, No. 2, pp. 360-367, Mar.-Apr. 1991.
Rozanova, E.P. et al. "Microbiological Processes in a High-Temperature Oil Field", Microbiology, v. 70, No. 1, pp. 102-110, 2000.
Schoell, Martin "Genetic Characteristics of Natural Gases" The American Association of Petroleum Geologists Bulletin, Dec. 1983, p. 2225-2238, vol. 67, No. 12.
Schoell, Martin et al. "Natural Sites of Bio-Conversion of CO2 and Hydrocarbons in the Subsurface: San Juan Basin and Michigan Basin" 2001 AAPG Annual Convention, Jun. 3-6, 2001, p. A180, abstract only.

Scott, A.R., Intergas'95, "Limitations and Benefits of Microbiallly Enhanced Coalbed Methane"; May 15-19, 1995—The University of Alabama Tuscaloosa, 10 pages, 1995.

Scott, Andrew R. "Composition and Origin of Coalbed Gases from Selected Basins in the United States" Proceedings of the 1993 International Coalbed Methane Symposium, University of Alabama/Tuscaloosa, May 7-12, 1993; pp. 207-222.

Scott, Andrew R. "Improving Coal Gas Recovery with Microbially Enhanced Coalbed Methane" in Coalbed Methane: Scientific, Environmental and Economic Evaluation; Eds. M. Mastaletcz, M. Glikson, and S. Golding, 1999, pp. 89-110, Kluwer Academic Publishers, Netherlands.

Scott, Andrew R. "Review of Key Hydrogeological Factors Affecting Coalbed Methane Producibility and Resource Assessment" Oklahoma Coalbed-Methane Workshop, 1999, pp. 12-36.

Scott, Andrew R. et al. "A New Energy Resource: Microbially Enhanced Gas Generation" 2001 AAPG Annual Convention, Jun. 3-6, 2001, p. A182, abstract only.

Scott, Andrew R. et al. "Composition, distribution, and origin of Fruitland Formation and Pictured Cliffs Sandstone gases, San Juan basin, Colorado and New Mexico", in S.D. Schwochow, D.K. Murray, and M.F. Fahy, eds., Coalbed methane of western North America: Denver, Rocky Mountain Association of Geologists, 1991, p. 93-108.

Scott, Andrew R. et al. "Limitations and Benefits of Microbially Enhanced Coalbed Methane" International Unconventional Gas Symposium (INTERGAS), May 15-19, 1995; pp. 423-432.

Scott, Andrew R. et al. "Microbially Enhanced Coalbed Methane: Limitations and Possible Benefits" AAPG Convention, 1995, p. 86A, abstract only.

Scott, Andrew R. et al. "Relation between basin hydrology and Fruitland gas composition, San Juan Basin, Colorado and New Mexico" Methane From Coal Seams Technology, Nov. 1991, pp. 10-18, vol. 9, No. 1.

Scott, Andrew R. et al. "Thermogenic and Secondary Biogenic Gases, San Juan Basin, Colorado and New Mexico—Implications for Coalbed Gas Producibility" AAPG Bulletin, Aug. 1994, v. 78, No. 8, pp. 1186-1209.

Smith, John W. et al. "Microbial Origin of Australian Coalbed Methane" AAPG Bulletin, vol. 80, No. 6 (Jun. 1996), pp. 891-897.

Smith, John W. et al. "The Stable Isotope Geochemistry of Australian Coals" Org. Geochem. vol. 3, 1982, pp. 111-131.

Springer, E. et al. "Partial Gene Sequences for the A Subunit of Methyl-Coenzyme M Reductase (Mcrl) as a Phylogenetic Tool for the Family Methanosarcinaceae", International Journal of Systematic Bacteriology, 1995, pp. 554-559.

Takashima, M. et al. "Mineral Requirements for Methane Fermentation" Critical Reviews in Environmental Control, vol. 19, Issue 5 (1990) pp. 465-479.

Um, Y., "Isolation and characterization of polycyclic aromatic hydrocarbon-degrading microorganisms under methanogenic conditions," Dissertation, Universtity of Maryland, 2004, pp. 1-99.

Volkwein, J.C. et al. "Biological Production of Methane from Bituminous Coal", Fuel Processing Technology, v. 40, pp. 339-345, 1994.

Weiner, J. M., and Lovley, D. R. "Rapid Benzene Degradation in Methanogenic Sediments from a Petroleum-Contaminated Aquifer", Appl. Environ. Microbiology 1998, vol. 64, No. 5, pp. 1937-1939.

Wellsbury, Peter et al. "Deep Marine biosphere fuelled by increasing organic matter availability during burial and heating" Nature 388, 573-576 (Aug. 7, 1997).

Whitfield, John "Origins of life: Born in a watery commune" Nature, (Feb. 19, 2004) pp. 674-676, vol. 427.

Whiticar, Michael J. "Correlation of natural gases with their sources" In: Magoon L. and W. Dow (eds.) The Petroleum System From Source to Trap, AAPG Spec. Publ. Memoir 60, 1994, Ch. 16, 261-83.

Whiticar, Michael J. et al. "Biogenic methane formation in marine and freshwater environments: $CO_2$ reduction vs. acetate fermentation—Isotope evidence" Geochimica et Cosmochimica Acta, 1986, pp. 693-709, vol. 50, No. 5.

Zengler et al., "Methane Formation From Long-Chain Alkanes by Anaerobic Microorganisms," Nature, vol. 401, pp. 266-269, Sep. 16, 1999.

Zobell, C.E., "Bacterial Release of Oil From Sedimentary Materials," The Oil & Gas Journal, pp. 62-65, Aug. 2, 1947.

THERMACETOGENIUM PHAEUM CONSORTIUM FOR THE PRODUCTION OF MATERIALS WITH ENHANCED HYDROGEN CONTENT

CROSS-REFERENCES TO RELATED APPLICATIONS

This application is a division of U.S. patent application Ser. No. 11/330,759, filed Jan. 11, 2006, entitled "THERMACETOGENIUM PHAEUM CONSORTIUM FOR THE PRODUCTION OF MATERIALS WITH ENHANCED HYDROGEN CONTENT," the entire disclosure of which is incorporated herein by reference.

FIELD OF THE INVENTION

The invention relates generally to the development of microbial consortium of microorganisms that can be used in formation environments to enhance metabolism of complex organic substrates (e.g. oil) into simpler compounds, such as methane. The invention also relates to methods of isolating microorganisms such as *Thermacetogenium phaeum* from their native environments.

BACKGROUND OF THE INVENTION

The United States and the rest of world are increasingly relying on natural gas for heating homes and buildings, generating electric power for residential and industrial applications, and as a feedstock for a variety of synthetic organic chemicals. Future demand for natural gas could grow even more dramatically as more new cars and trucks use electric power. Natural gas will likely play a major role in generating the electricity used in charging vehicle batteries, and supplying the methane and hydrogen used in operating vehicle fuel cells. Because the already high demand for natural gas is expected to soar, concerns about supply are growing.

One proposed solution is to build more long haul infrastructure to move natural gas where demand is greatest. Because natural gas is a gas at room temperature, there are more challenges in transporting it than for fuels like oil, coal and gasoline. The current leading proposal is to cool the gas to temperatures where it liquefies and transport the liquid natural gas ("LNG") on refrigerated tankers. At the destination port, the LNG is warmed back into a gas that gets fed into the existing gas pipeline infrastructure. This proposed solution has been criticized for a number or reasons, including the significant cost associated with condensing and transporting LNG. There are also serious safety concerns about accidents and sabotage to the LNG infrastructure. These concerns have lead to strong local opposition to proposed sites for building a LNG port. In addition, some have argued that importing LNG only increases dependence on foreign sources of natural gas from politically unstable regions.

Another proposed solution is to explore and develop more sites for local natural gas production. In the United States, one site believed to contain large, untapped reserves of natural gas is the Arctic National Wildlife Refuge ("ANWR") in Alaska. But proposals to develop this site, as well as other sites in the Rocky Mountain region of the United States, have been strongly opposed by environmental groups. Thus, development of new sources of local natural gas also faces significant limitations.

One way to avoid the problems with importing natural gas and developing new sites is to enhance gas production from existing local sites. One promising technology for doing this is microbially enhanced methane production. This technology uses microorganisms to metabolize complex organic substrates such as oil or coal into simpler compounds like methane and hydrogen. Stimulating the right indigenous microorganisms or introducing the right microorganisms under the right conditions to "retired" oil fields and coal deposits that are too deep to mine could turn these sites into productive new sources of domestic natural gas.

Because only a small fraction of the oil and coal was recovered from these sites while they were operating, the amount of hydrocarbon substrate still available for microbial conversion is enormous. The mature coal mines in the Powder River Basin in Wyoming, for example, are still estimated to have 1,300 billion short tons of unmined coal. If just 1% of this coal could be microbially converted into natural gas, it could supply the current annual natural gas need of the United States for four years. This story could be repeated at many other mature coal and oil sites across the country.

But the technology of microbial natural gas generation is still in its infancy. Many of the microorganisms require an anoxic or microoxic environment and are difficult to study in a conventional microbiology laboratory. While metabolic pathways have been postulated for breaking down a complex hydrocarbon substrate into natural gas and hydrogen, few specific microorganisms that are involved in methanogenic hydrocarbon biodegradation have been positively identified. The "first bite" microorganisms, which start the initial breakdown of complex hydrocarbon substrate into smaller molecules, have been particularly elusive.

Thus, there is a need for identifying microorganisms involved in biogenic gas production in underground hydrocarbon formations such as coal mines and oil fields. The identity of these microorganisms will provide valuable insight into how complex hydrocarbons are converted into fuel gases like hydrogen and methane. This insight can lead to methods of isolating, cultivating, and stimulating the microorganisms to make fuel gases at commercially viable production rates. These and other issues are addressed by the present invention.

BRIEF SUMMARY OF THE INVENTION

Embodiments of the invention include isolated microbial consortium. The consortium include a first microbial consortium that has *Thermacetogenium phaeum* to metabolize a complex hydrocarbon substrate into metabolic products comprising an acetate compound. The consortium may also include a second microbial consortium that has a methanogen to convert the acetate compound into a final product comprising methane.

Embodiments of the invention may also include methods of increasing production of materials with enhanced hydrogen content. The methods may include the steps of isolating *Thermacetogenium phaeum* from geologic formation water, and culturing the isolated *Thermacetogenium phaeum* to increase the *Thermacetogenium phaeum* population. The methods may further include introducing a consortium comprising the cultured *Thermacetogenium phaeum* into a hydrocarbon formation containing a complex hydrocarbon substrate.

Embodiments of the invention still further include methods of isolating *Thermacetogenium phaeum* from a native consortium of microorganisms. The methods may include the steps of removing formation water from an underground formation, where the formation water includes the native consortium that includes the *Thermacetogenium phaeum*. The methods may also include heating the formation water to about 120° C. or more, where the *Thermacetogenium phaeum*, including its spores, survives the heating process. The heating may cause at least some of the *Thermacetogenium phaeum* to form spores (i.e., to sporulate).

Embodiments of the invention still also include methods of stimulating biological activity of *Thermacetogenium phaeum* in a geologic formation. The methods may include the steps of detecting the *Thermacetogenium phaeum* in the geologic formation, measuring one or more environmental characteristics of the geologic formation, and determining a composition of carbonaceous material in the formation. The methods may also include adding an amendment to the formation based on the measurements of the environmental characteristics and the composition of the carbonaceous material.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

DETAILED DESCRIPTION OF THE INVENTION

*Thermacetogenium phaeum* ("*T. phaeum*") is identified as a "first bite" microorganism that can metabolize part of a complex hydrocarbon substrate such as crude oil into a fermentation end product such as acetate (e.g., acetic acid) or formate (e.g., formic acid). Thus, *T. phaeum* appears to play dual roles in a metabolic process of converting complex hydrocarbons to methane: The microorganism appears to be responsible for the hydrolytic fermentation of the starting hydrocarbon to an intermediate, and also for converting that intermediate into acetate. After this, all that remains is to convert the acetate into methane with a methanogen. The acetate can be converted directly to methane. Alternatively, a syntrophic microorganism can convert the acetate to hydrogen gas and carbon dioxide, which is utilized by hydrogen utilizing methanogens. Thus, a process for metabolizing a complex hydrocarbon into methane has been discovered that requires only two or three species of anaerobic microorganisms.

The discovery of a two member consortium for biogenic gas production means that processes of stimulating biogenic gas production may be simpler than previously thought. Metabolic processes that require participation from several species of microorganisms increase the chances for a bottleneck when the metabolism of one species starts to decline. In addition, environmental changes, such as a change in temperature, nutrient availability, inhibitor accumulation, pH, etc., that stimulate the participation of one species in the metabolic process may hurt participation by others. When fewer species are used, there's an increased chance for the successful and prolonged stimulation of methane or hydrogen formation in subsurface formations.

Embodiments of the invention include a consortium of isolated microorganisms that may require two species to metabolize a complex hydrocarbon substrate like oil into biogenic gases like methane or hydrogen. One member of this consortium is *T. phaeum* and a second member may be a methanogen such as a Methanobacteriales, Methanomircobacteria, Methanopyrales, Methanococcales, Methanosaeta, etc. The consortium may also include additional microorganism species that provide additional metabolic pathways to the final products. For example, the consortium may include multiple species of methanogens: One species can convert the acetate produced by *T. phaeum* directly into methane and carbon dioxide though an acetate fermentation process. Another species can combine the carbon dioxide with hydrogen to produce methane and water via a carbonate reduction. Additional details on the role of *T. phaeum* in metabolic processes to convert a complex hydrocarbon substrate to materials with an enhanced hydrogen content will now be described.

Biogenic Processes of Making Materials with Enhanced Hydrogen Content

Figure 1:
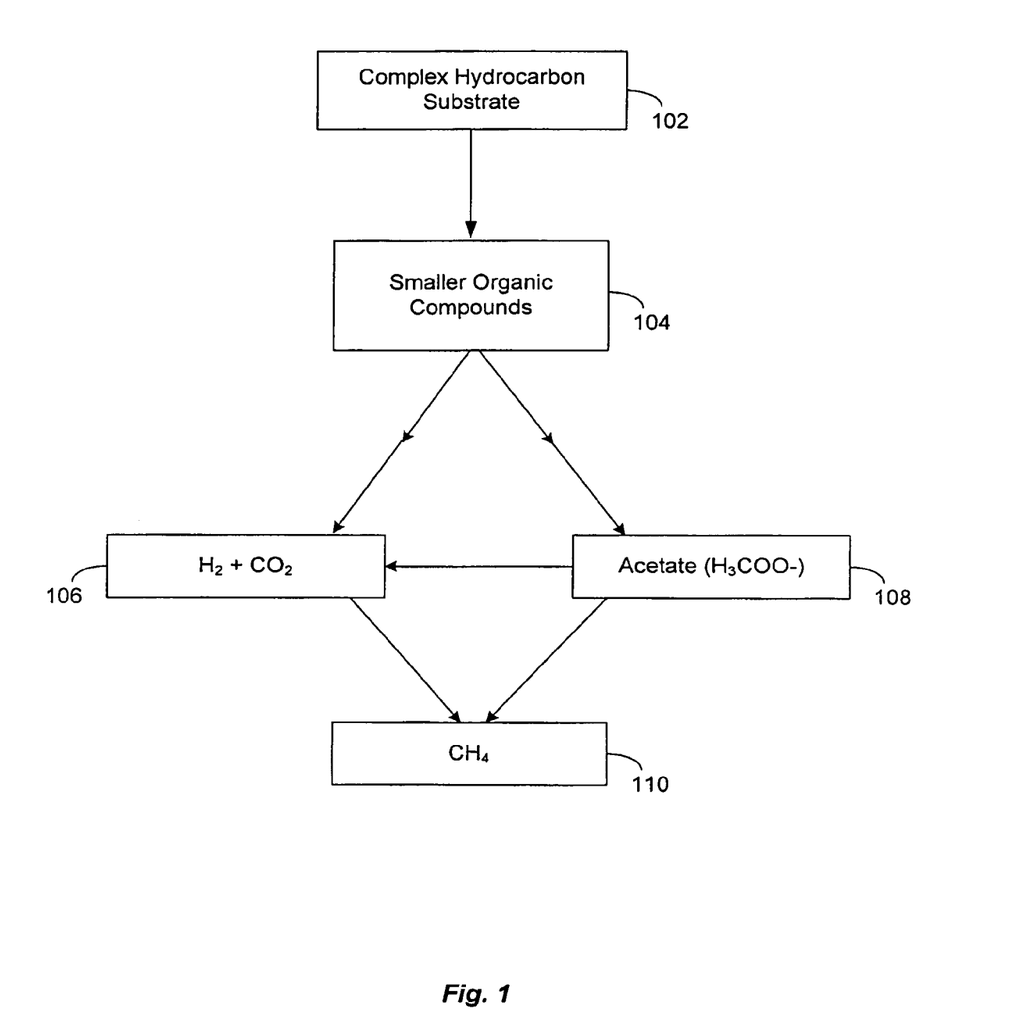
FIG. 1 shows a simplified schematic of a three-stage anaerobic conversion of a complex hydrocarbon substrate to a material with an enhanced hydrogen content.

FIG. 1 shows a simplified schematic of a three-stage anaerobic conversion of a complex hydrocarbon substrate to a material with an enhanced hydrogen content. Additional details about three stage metabolic processes may be found in co-assigned U.S. patent application Ser. No. 11/099,881, titled "GENERATION OF MATERIALS WITH ENHANCED HYDROGEN CONTENT FROM ANAEROBIC MICROBIAL CONSORTIA"; and U.S. patent application Ser. No. 11/099,880, titled "GENERATION OF MATERIALS WITH ENHANCED HYDROGEN CONTENT FROM MICROBIAL CONSORTIA INCLUDING THERMOTOGA," of which the entire contents of both applications is herein incorporated by reference for all purposes.

FIG. 1 shows the conversion starting with a complex hydrocarbon substrate 102 being metabolized into smaller hydrocarbon products. The complex hydrocarbon substrate may be oil, coal, coke, kerogen, anthracite, coal tar, bitumen, lignite, peat, carbonaceous shale, and sediments rich in organic matter, among other kinds of carbonaceous material. The substrate may also be organic polymers and polyaromatics.

A "first bite" microorganism metabolizes at least a portion of the substrate into smaller organic compounds 104. The metabolic reaction may involve the hydrolytic fermentation of the organic substrate into smaller-sized organic metabolites. These metabolites may be converted by additional anaerobic microorganisms to even smaller-sized molecules, including carbon dioxide, hydrogen, ammonia, sulfides, and acetate 108.

In the final stages, methanogens may convert the acetate (or hydrogen and carbon dioxide 106) into methane 110. Methanogen metabolism of acetate may involve an acetate fermentation process that may be represented by the chemical reaction formula:

$$CH_3COO^- + H^+ \rightarrow CH_4 + CO_2$$

The methanogen metabolism of hydrogen and carbon dioxide may involve a carbonate reduction process that may be represented by the chemical formula:

$$CO_2 + 4H_2 \rightarrow CH_4 + 2H_2O$$

A single species of methanogen in the consortium may be able to perform both processes, depending on the concentration of acetate, hydrogen and carbon dioxide in the reaction environment. Alternatively, multiple species of methanogens may be present in the consortium, some doing acetate fermentation and some doing carbonate reduction.

In embodiments of the present invention, the "first bite" of the hydrocarbon substrate and the metabolism of the smaller hydrocarbon product are catalyzed by a single microorganism. *T. phaeum* has been identified as taking a complex hydrocarbon substrate such as crude oil and metabolizing at least a portion of it into acetate. A second consortium member, a methanogen such as *Methanosarcina thermophila*, may metabolize the acetate into methane. Thus, a consortium with just two species of microorganisms, one of which is *T. phaeum*, may be used to metabolize a complex hydrocarbon substrate into methane.

Figure 2A:
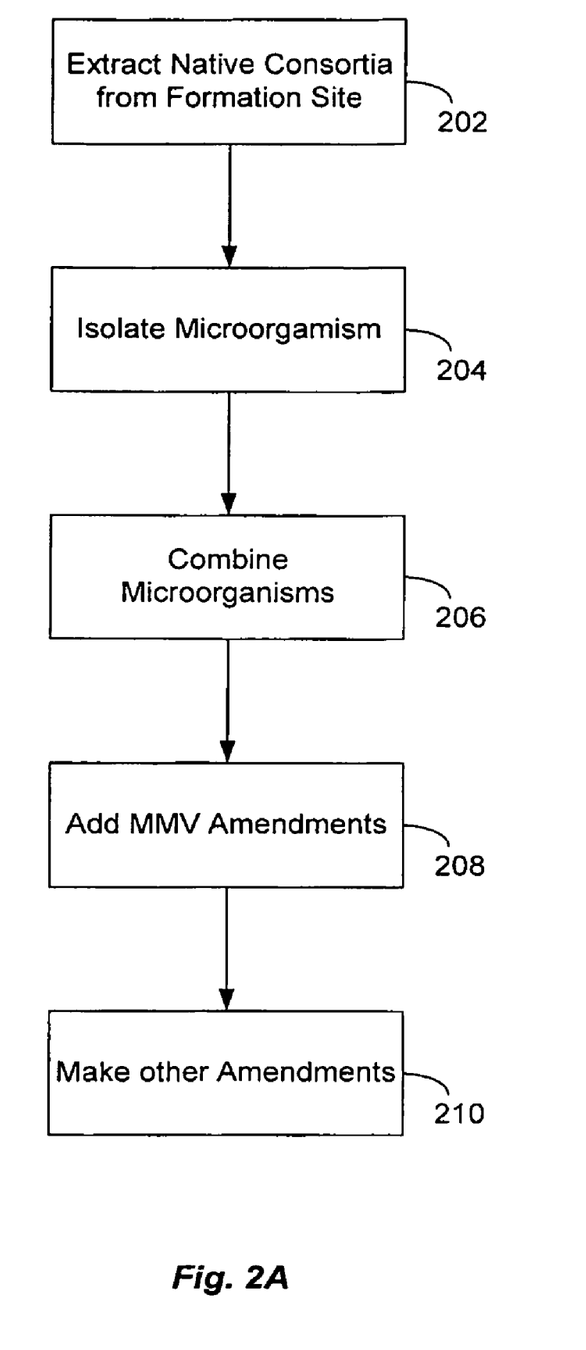
FIG. 2A is a flowchart illustrating steps in methods of isolating and preparing a consortium of microorganisms according to embodiments of the invention.

Referring now to FIG. 2A, steps in methods of isolating *T. phaeum* and preparing a consortium that includes the microorganism according to embodiments of the invention is described. The method includes extracting samples from a formation site 202 that contain a native consortium of microorganisms. The samples may be taken from solid substrate and/or formation water at the site. When consortium microorganisms include obligate anaerobes, additional steps may be taken to isolate the samples in a low oxygen environment. These steps may include sealing the sample in a container that has been purged of air and filled with an atmosphere of nitrogen, helium, argon, etc. The containers may remained sealed until being opened in an anaerobic glove box for further processing and study.

The formation site samples may be transported to a preparation site, such as a laboratory, so the *T. phaeum* in the native consortium can be isolated 204. This may include filtering samples of native formation water to concentrate the microorganisms in the sample. For example, a sample of native formation water may be centrifuged through a filter having pores that are small enough to trap most microorganism consortium members on the filter. A portion of the filtered formation water may be added back to the filtrate to create a concentrated suspension of the native consortium.

The samples may be autoclaved to kill or inactivate native microorganisms other than *T. phaeum*. For example, autoclaving a sample of formation water at 120° C. for about 20 minutes has been shown to inactivate methanogens in a *T. phaeum* consortium. The autoclaving process may include two, three, or more autoclaving cycles where the sample is repeatedly raised to the peak autoclaving temperature before being lowered back down to room temperature. The *T. phaeum* itself survives the autoclaving to give an autoclaved sample product of isolated *T. phaeum*.

The consortium that includes the *T. phaeum* isolate may be combined with one or more additional microorganic consortia 206 to create the isolated microbial consortium that can metabolize complex hydrocarbon substrates to materials with enhanced hydrogen content, such as methane and hydrogen. These additional microorganisms may include *Thermotogas* like *Thermotoga hypogea*. Other microorganisms that may be included in the isolate may be from genera including *Gelria, Clostridia, Moorella, Thermoacetogenium, Pseudomonas*, and/or *Methanobacter*, among others.

Amendments may also be added to the isolated consortium that stimulate the metabolism of the hydrocarbon substrates. The amendments may include the addition of minerals, metals, and/or vitamins ("MMV") to the isolate 208. Examples of mineral amendments may include the addition of chloride, ammonium, phosphate, sodium, magnesium, potassium, and/or calcium to the isolate, among other kinds of minerals. Metal amendments may include the addition of manganese, iron, cobalt, zinc, copper, nickel, selenate, tungstenate, and/or molybdate to the isolate, among other kinds of metals. Vitamin amendments may include the addition of pyridoxine, thiamine, riboflavin, calcium pantothenate, thioctic acid, p-aminobenzoic acid, nicotinic acid, vitamin B12, 2-mercaptoehanesulfonic acid, biotin, and/or folic acid, among other vitamins. The addition of these amendments may involve adding mineral salts, metal salts, and vitamins directly to the isolate, or first preparing a solution of the salts and vitamins that then gets added to the isolate. The concentration of the MMV amendment may depend on the concentration and composition of an isolated consortium. Examples of concentration ranges for amendment components may include about 1 mg/L to about 500 mg/L for mineral amendment; about 10 μg/L to about 2000 μg/L for a metal amendment; and about 1 μg/L to about 100 μg/L for a vitamin amendment.

Other amendments may be made to the isolated consortium 210. For example, yeast extract may be added to the isolates, and the pH and/or temperature of the isolates environment may be adjusted.

Figure 2B:
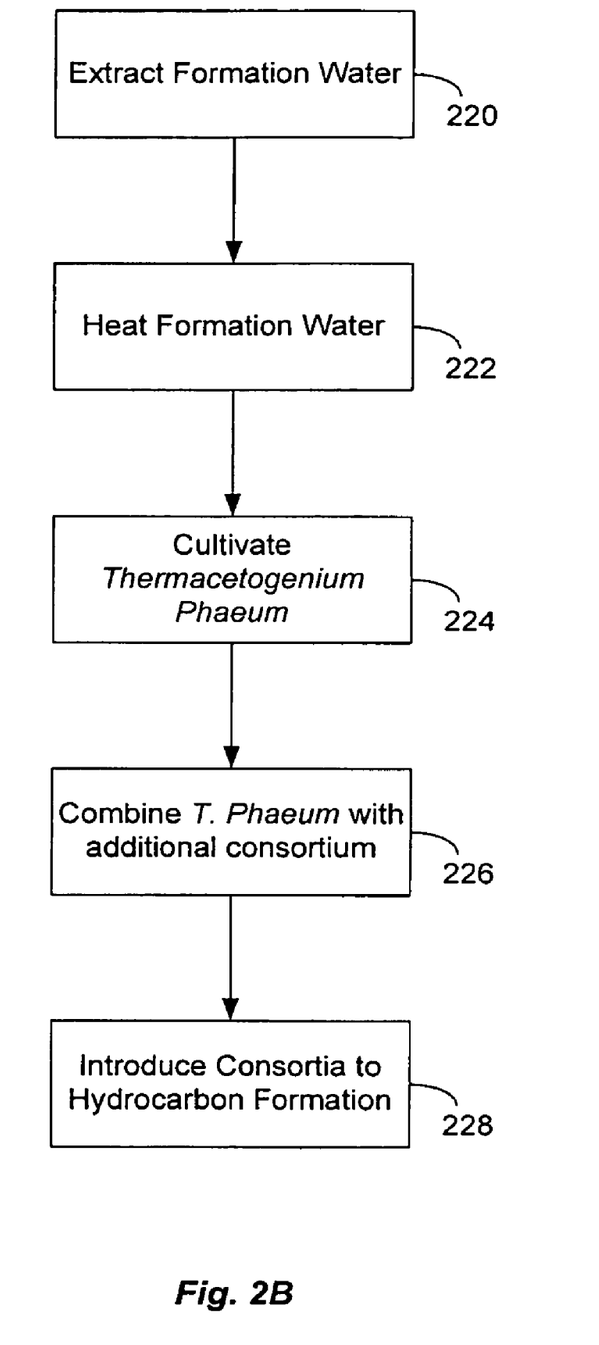
FIG. 2B is a flowchart illustrating steps in method of extracting formation water and introducing consortia to hydrocarbon formations according to embodiments of the invention.

FIG. 2B shows another flowchart that includes steps in a method of isolating *T. phaeum* and making a consortium according to embodiments of the invention. The method includes extracting formation water 220 that includes *T. phaeum* and other microorganism species. The formation water is heated 222 to a temperature that neutralizes (e.g., kills) microorganisms in the water other than *T. phaeum*. The heating 222 may cause the *T. phaeum* to form spores that can survive larger variations in environmental conditions than active *T. phaeum*.

Heating the formation water 222 may create an isolate or concentrate of *T. phaeum* by neutralizing the other microorganisms present. Additional isolation steps may also be done to further concentrate and/or purify the *T. phaeum*, such as filtering the *T. phaeum* from other components in the water. The *T. phaeum* may then be cultivated 224 to increase the amount of microorganism that gets introduced to the hydrocarbon formation. Cultivation may include germinating *T. phaeum* spores into active microorganisms that can grow in a nutrient rich environment that stimulates population growth. The environment may also include hydrocarbon substrates that are taken from the formation where the *T. phaeum* will be introduced. Cultivating the *T. phaeum* on the same substrate may bias growth towards those the members of the *T. phaeum* population that are most efficient at utilizing the substrate as a nutrient source.

The cultivated *T. phaeum* may be forced into a dormant phase (i.e., spores) before being stored and/or transported to an introduction site. Spore formation may be accomplished by heating the *T. phaeum* and/or removing at least some of the water from the micoorganism's surrounding environment. The *T. phaeum* spores can withstand larger variations in environmental conditions (e.g., temperature, hydration, nutrient concentrations, pH, salinity, etc.) than the active microorganisms, making them easier to store and transport.

A consortium that includes the cultivated *T. phaeum* may be combined with additional consortia of microorganisms 226 to form a consortium of microorganisms that includes *T. phaeum*. The additional consortia may include one or more methanogenic microorganism species (e.g., *Methanosarcina thermophila* and *Methanosaeta thermophila*, etc.).

The combination of the *T. phaeum* consortium with additional consortia may take place before or after the *T. phaeum* is stored and transported to the formation site where the consortium is introduced 228. The *T. phaeum* consortium may also be combined with the additional consortia in situ in the hydrocarbon formation. For example, a *T. phaeum* consortium and one or more additional consortia may be introduced to the formation in different injection steps and afterwards combine into the final microorganic consortium.

The *T. phaeum* may be introduced to the hydrocarbon formation 228 as active microorganisms or as spores that can germinate in situ in the formation environment. The introduction may also include a nutrient amendment that depends on whether the active microorganisms or the spores are being introduced into the hydrocarbon formation. The temperature, pH, salinity, and other environmental parameters of the *T. phaeum* consortium may also depend on whether the *T. phaeum* is introduced as active microorganisms or spores.

Figure 3:
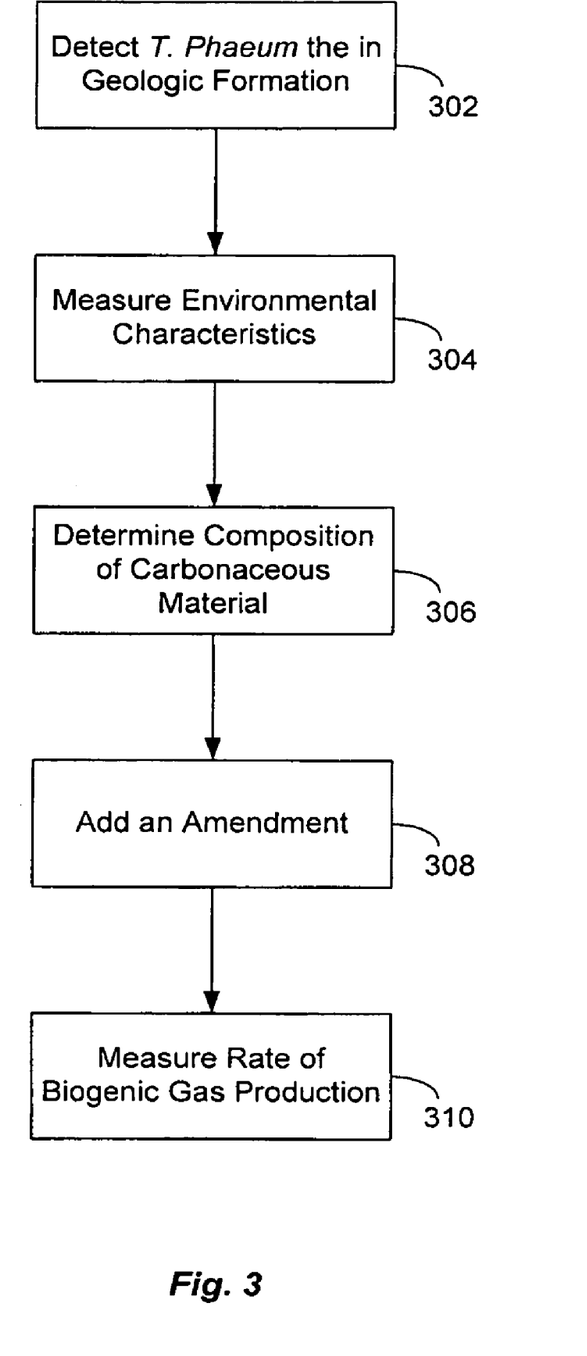
FIG. 3 is a flowchart of steps in methods of stimulating biological activity of *Thermoacetogenium Phaeum* according to embodiments of the invention.

Referring now to FIG. 3, steps in a method of in situ stimulation of biological activity of *T. phaeum* in a geologic formation according to embodiments of the invention are shown. The method may include detecting the *T. phaeum* in the formation 302. Detection may be done by extracting a sample from the formation and bringing it to a lab to test for a genetic match, or conducting tests at the formation site. The method may also include measuring environmental characteristics in the formation 304. These may include temperature, pH, Eh, salinity, atmospheric composition, mineralogy, alkalinity, and concentrations of nutrients, vitamins, inorganic elements, terminal electron acceptors, and substances that are known to be toxic to *T. phaeum*, among other characteristics of the formation environment.

The method may also include the determination of the composition of carbonaceous material the *T. phaeum* may use as a substrate. This determination may include the breakdown of major hydrocarbon constituents of an oil, coal, etc. It may also include an elemental analysis of the amount of carbon, oxygen, hydrogen, nitrogen, phosphorous, sulfur, metals, etc., present in the material.

The data obtained from the measurements of the environmental characteristics of the formation 304 and composition of the carbonaceous material 306 provides information about the types of amendments that are most likely to stimulate in situ biological activity of the *T. phaeum* in the formation. The biological activity may include increased population growth of *T. phaeum* relative to other microorganisms in the native microorganism consortium of the formation. It may also include stimulating the rate of metabolic activity of the *T. phaeum* in the formation.

An amendment with a high probability of stimulating biological activity may be added to the formation 308. These amendments may include adding a *T. phaeum* growth stimulant, such as a pyruvate (e.g., sodium pyruvate), to the formation. Amendments may also include adding a compound that is a known nutrient for *T. phaeum*. These may include alkyl alcohols such as methanol, ethanol, n-propanol, n-butanol, etc. They may also include diols, such as 2,3-butanediol, as well as other hydrocarbons such as ethanolamine, 3,4,5-trimethoxybenzoate, syringate, vanillate, glyine, cysteine, and formate. They may further include hydrogen and carbon dioxide. Amendments may also include the addition of more water to the formation environment to lower the salinity or to spread the in situ *T. phaeum* over a larger region of the carbonaceous material. They may also include localized increases in the temperature of the formation environment.

The method may also include measuring the rate of biogenic gas production 310 after the amendment is added to the formation. These measurements may involve measuring changes in total gas pressure in the formation, or changes in the partial pressure of a particular gas, such as methane, hydrogen, carbon monoxide, carbon dioxide, etc. An increase in the presence of a desired product, such as hydrogen and/or methane may indicate that the degree to which the amendment is stimulating biological activity of the *T. phaeum*. These data may be used to determine if additional amendments should be made to the formation to further stimulate the *T. phaeum*.

Definitions

The consortium of microorganisms and methods of using them to make biogenic materials with enhanced carbon content described here straddle the arts of microbiology, molecular biology, organic chemistry, and oil and gas recovery, among others. Consequently, some of the terms used here may have slightly different meanings in the different arts. Therefore some definitions are provided to clarify the meaning of some terms used to describe the present invention.

"Microorganism," as used here, includes bacteria, archaea, fungi, yeasts, and molds. Sometimes a microorganism can have defining characteristics from more than one class, such as a combination of bacteria and fungi. The term microorganism as used here also encompasses these hybrid classes of organisms.

"Anaerobic microorganisms," as used here, refers to microorganisms that can live and grow in an atmosphere having less free oxygen than tropospheric air (i.e., less than about 18%, by mol., of free oxygen). Anaerobic microorganisms include organisms that can function in atmospheres where the free oxygen concentration is less than about 10% by mol., or less than about 5% by mol., or less than about 2% by mol., or less than about 0.5% by mol.

"Facultative anaerobes," as used here, refer to microorganisms that can metabolize or grow in environments with either high or low concentrations of free oxygen.

"Methanogen," as used here, refers to obligate and facultative anaerobic microorganisms that produce methane from a metabolic process. Two metabolic pathways commonly seen in methanogens are acetate fermentation, where acetate and a hydrogen ion are metabolized into methane and carbon dioxide, and carbonate reduction, where carbon dioxide and molecular hydrogen are metabolized into methane and water. Classes of methanogens include Methanobacteriales, Methanomicrobacteria, Methanopyrales, Methanococcales, and Mathanosaeta (e.g., *Mathanosaeta thermophila*), among others. Specific examples of methanogens include *Thermotoga hypogea, Thermotoga lettingae, Thermotoga subterranean, Thermotoga elfii, Thermotoga martima, Thermotoga neapolitana, Thermotoga thernarum*, and *Thermotoga petrophila, Methanobacter thermoautotorophicus, Methanobacter wolfeii*. Methanogens may also produce methane through metabolic conversion of alcohols (e.g., methanol), amines (e.g., methylamines), thiols (e.g., methanethiol), and/or sulfides (e.g., dimethyl sulfide). Examples of these methanogens include methanogens from the genera *Methanosa-*

*rcina* (e.g., *Methanosarcina barkeri, Methanosarcina thermophila, Methanosarcina siciliae, Methanosarcina acidovorans, Methanosarcina mazeii, Methanosarcina frisius*); *Methanolobus* (e.g., *Methanolobus bombavensis, Methanolobus tindarius, Methanolobus vulcani, Methanolobus taylorii, Methanolobus oregonensis*); *Methanohalophilus* (e.g., *Methanohalophilus mahii, Methanohalophilus euhalobius*); *Methanococcoides* (e.g., *Methanococcoides methylutens, Methanococcoides burtonii*); and/or *Methanosalsus* (e.g., *Methanosalsus zhilinaeae*). They may also be methanogens from the genus *Methanosphaera* (e.g., *Methanosphaera stadtmanae* and *Methanosphaera cuniculi*, which are shown to metabolize methanol to methane). They may further be methanogens from the genus *Methanomethylovorans* (e.g., *Methanomethylovorans hollandica*, which is shown to metabolize methanol, dimethyl sulfide, methanethiol, monomethylamine, dimethylamine, and trimethylamine into methane).

"Materials with enhanced hydrogen content," as used here, means organic products that have a higher ratio of C—H to C—C bonds than the organic compounds from which they were derived. These materials will also have a higher mol. % hydrogen than found in the compounds from which they were derived. For example, acetic acid has the chemical formula $CH_3COOH$, representing 2 carbon atoms, 2 oxygen atoms, and 4 hydrogen atoms, to give a total of 8 atoms. Since 4 of the 8 atoms are hydrogen, the mol. % of hydrogen atoms in acetic acid is: (4 Hydrogen Atoms)/(8 Total Atoms)=0.5, or 50%, by mol. (or on a molar basis). Methane has the chemical formula $CH_4$, representing 1 carbon atom and 4 hydrogen atoms, making a total of 5 atoms. The mol. % of hydrogen atoms in methane is (4 Hydrogen Atoms)/(5 Total Atoms)=0.8, or 80%, by mol. Thus, the conversion of acetic acid to methane increases the mol. % of hydrogen atoms from 50% to 80%. In the case of molecular hydrogen, the mol. % of hydrogen atoms is 100%.

"Hydrocarbon," as used here, means molecules that contain carbon and hydrogen atoms. Optionally, the molecules may also have nitrogen, sulfur, phosphorous, and/or oxygen atoms, among other atomic species.

"Complex Hydrocarbon Substrates," as used here, include compounds found in geologic deposits of carbonaceous material. These may include coal, oil, kerogen, peat, lignite, oil shale, tar sands, bitumen, and tar.

Experimental

Figure 4A:
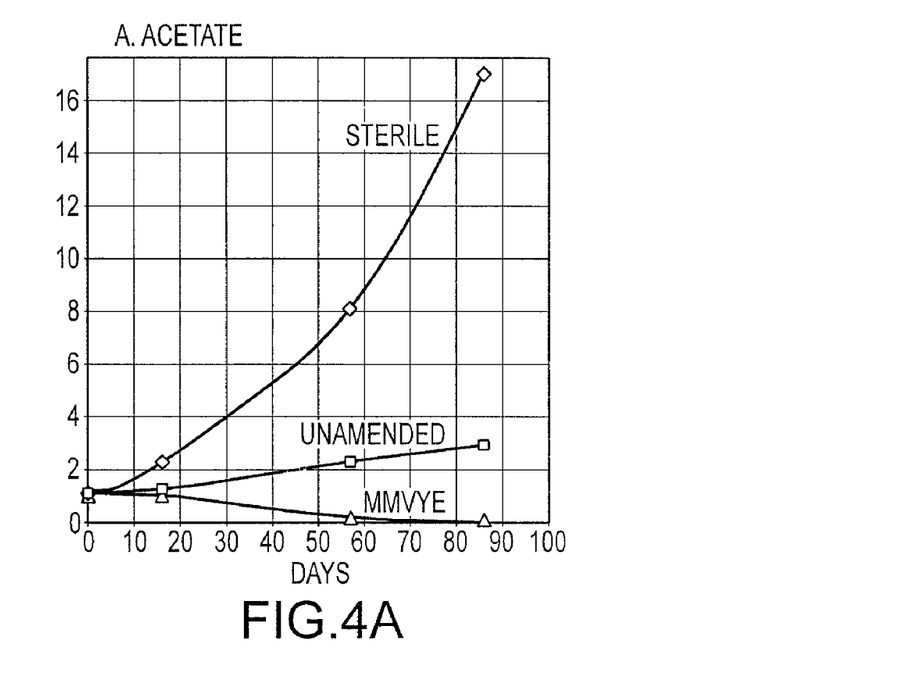
FIG. 4A is a graph showing the accumulation of acetate in a formation water sample.
Figure 4B:
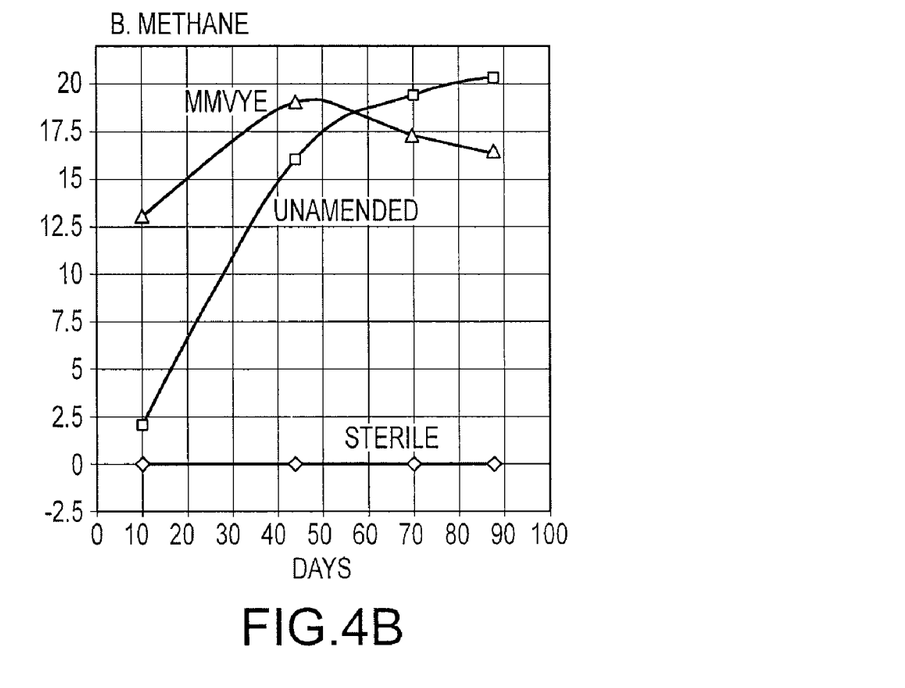
FIG. 4B is a graph showing the accumulation of methane in a formation water sample.

During a course of experiments to characterize metabolic activity of a native microorganism consortium, a surprising result was observed. FIG. 4A charts the robust production of acetate that was measured from several control samples of native formation water and oil that was autoclaved to kill the microorganisms. FIG. 4B shows that non-autoclaved oil and water incubations did not generate acetate concentrations as high as the autoclaved incubations. At first, the presumption was that acetic acid present in the oil was escaping into the formation water of the sample bottles. But testing revealed almost no acetate was present in the samples. Thus, an abiotic source for the observed acetate production seemed unlikely.

Additional examination of the autoclaved formation water samples was done, including filtration of the formation water and examination of the filtered cells with phase-contrast microscopy. Rod-shaped microorganisms were observed in the autoclaved formation water, suggesting at least one species was able to survive the autoclaving conditions.

But apparently not all the species in the native consortium survived autoclaving. Methanogenesis was observed in the non-autoclaved samples and produced much less acetate than the autoclaved samples (see FIG. 5). This suggested that the methane producing microorganisms were acetate utilizing methanogens that metabolized the acetate into methane. It also suggested that autoclaving was effective at killing the methanogens, but not the acetate generating species.

A Terminal Restriction Fragment Length Polymorphism (TRFLP) analysis of the 16S rDNA was run to identify the species that survived the autoclaving and produced the acetate. The TRFLP analyses of the autoclaved samples that produced acetate showed only one significant band. Sequencing of this 16S rDNA band revealed that it was the 16S rDNA gene of *Thermacetogenium phaeum* (*T. phaeum*). This suggested *T. phaeum* was the sole active microbial species in the autoclaved sample.

This conclusion is somewhat surprising because it suggests a single species can metabolize a complex hydrocarbon substrate to acetate. It's also one of the few instances where a "first bite" anaerobic microorganism that is responsible for the initial metabolism of a complex hydrocarbon substrate (in this case crude oil) under methanogenic conditions (e.g., in the absence of electron acceptors including nitrate and sulfate) has been positively identified. The implication of this discovery is that a consortium of just two species of microorganisms can be constructed that can metabolize complex hydrocarbon substrates into methane. If only two species are necessary to do this, amendments can be developed to maximize the metabolic activity of the target species(s) without as much concern about their collateral effects on other species. Furthermore, since the role of the methanogen can be played by a variety of species, a single methanogen species (or group of species) can be selected that has the highest productivity when paired with *T. phaeum*.

Additional details of the experiments that lead to the discovery of *T. phaeum* as a first bite anaerobic microorganism are now described.

Testing Procedures Used with Formation Water Samples

Microbial Activity Experiments: Triplicate experimental incubations were prepared by adding ten ml of produced water collected from eleven oil-water separators and from a producing well (Nine Mile 4-6 wellhead) to 30 ml serum bottles while working in an anaerobic glove bag. 0.1 ml of oil from the respective sampling locations was added to the incubations. The headspace of the incubations was replaced with $N_2/CO_2$ (95/5).

Nutrient supplemented incubations received solutions of minerals, metals, vitamins, and yeast extract ("MMVYE") according to Table 1:

TABLE 1

| Composition of the MMVYE Nutritional Supplement | |
|---|---|
| Amendment Mineral Salts | Concentration Mineral Salt Concentration in mg/L |
| Chloride | 443 |
| Ammonium | 111 |
| Phosphate | 23.5 |
| Sodium | 103 |
| Magnesium | 9.9 |
| Potassium | 17.3 |
| Calcium | 3.6 |
| Metals | Metal Concentrations in µg/L |
| Manganese | 1600 |
| Iron | 570 |
| Cobalt | 250 |

TABLE 1-continued

Composition of the MMVYE Nutritional Supplement

| Zinc | 230 |
|---|---|
| Copper | 40 |
| Nickel | 20 |
| Selenate | 80 |
| Tungsten | 70 |
| Molybdate | 66 |

| Vitamins | Vitamin Concentrations in µg/L |
|---|---|
| Pyridoxine HCL | 40 |
| Thiamine | 20 |
| Riboflavin | 20 |
| Calcium pantothenate | 20 |
| Thioctic acid | 20 |
| p-aminobenzoic acid | 20 |
| Nicotinic acid | 20 |
| Vitamin B12 | 20 |
| 2-mercaptoehanesulfonic acid | 8 |
| Biotin | 8 |
| Folic acid | 8 |

Autoclaved control samples of formation water and oil were produced by autoclaving on three successive cycles of raised temperature and pressure. For each cycle the formation water sample was heated to 120° C. for 20 minutes under a pressure of 15 psi.

Methane, carbon dioxide, and hydrogen were quantified in the headspace of the incubations by gas chromatography with flame ionization detection ("GC-FID"). Organic acids in the fluid samples post-incubation were also quantified with GC-FID.

Quantification of Acetate in Oils: Five gram samples of several oils (Nine Mile 4-6 well head, Nine Mile 10-7, Monument Butte 12-35, Ashley 12-11, and Gilsonite 6-32) were added to serum bottles while working inside an anaerobic glove bag. The headspace was then exchanged with helium. The samples were brought to 60° C., and 10 ml of anoxic HPLC water was injected into the samples. The samples were shaken vigorously with a vortex placed inside the 60° C. incubator for thirty minutes. An aqueous sample was then obtained and analyzed for organic acids by gas chromatography.

Microscopic examination of microorganisms in the samples was done by recovering 0.4 ml of liquid from experimental bottles MBP-01 NE 100 ($H_2$+Min+Met+Vit+YE) and MBP-01 NE 092 (Sterile control) and centrifuging them through a sterile 0.2 um filter at 5000 rpm. 40 ul of supernatant was added back to the filter to suspend the cells. 20 µl of the concentrated cell suspensions was used for direct microscopic examination for microbial cells via phase-contrast microscopy. The remaining 20 µl was used to prepare a gram stain for microscopic examination via light microscopy.

TRFLP analysis of the samples was done by isolating a DNA fraction from microorganism cultures derived from each sample. Approximately 50 ng of consortium DNA was used in PCR reactions containing primers 519F (sequence 5'-CAGCMGCCGCGGTAATWC-3') and infrared-labeled (IR) 1406R (sequence 5'-ACGGGCGGTGWGTRCAA-3'). The 891 base pair product was gel purified and digested with the restriction enzyme Hha I. Digestion products were desalted, concentrated to 10 µl in a speedvac, and 4 µl was electrophoresed on an 8% polyacrylamide gel using the Li-Cor 4300 genetic analyzer. After PCR amplification the light exposure was minimized to avoid photobleaching the infrared label. After 30 minutes of electrophoresis predominant IR labeled bands were excised from the gel using the Li-Cor Odyssey and purified with the Qiaex II gel purification kit (Qiagen). An 18 base double-stranded linker (SL1 and SL1 complement) was ligated to the non-labeled end of the oligonucleotide, and DNA fragments were re-amplified using standard PCR techniques with primers SL1 and 1406R. PCR products were gel purified, and cloned using the Invitrogen TOPO TA cloning kit. Clones were sequenced using an IR-labeled 1492 primer and the SequiTherm EXCEL™ II DNA Sequencing Kit (Epicentre).

Experimental Results

FIG. 4A plots the accumulation of acetic acid (i.e., acetate) in the formation water oil-water incubations established with samples from the MB 12-35 production well. FIG. 4B plots methane for the same incubations. Significant accumulation of acetic acid was observed in MB 12-35 oil water incubations that were autoclaved. Methane was not produced in these autoclaved incubations. In contrast to the autoclaved oil-water incubations only slight acetate accumulation was observed in the unamended incubations, and the acetate concentration decreased in the nutrient amended incubations (presumably consumed by the methanogens). As FIG. 4B shows, rapid methanogenic activity was detected in MMVYE amended incubations, with greater than 12% methane accumulation prior to the first headspace sampling at 10 days. Methanogenic activity occurred at a slower rate in unamended incubations.

The plots in FIGS. 4A-B indicate that autoclaving was effective at killing methanogens. The accumulation of acetate in the unamended incubations indicates that acetate production outpaced acetate consumption. The addition of MMVYE stimulated acetate conversion to methane relative to the unamended controls suggesting that downstream metabolism, including methanogens, was nutrient limited.

The source of acetic acid production could not have been diffusion from the oil. Water extractable acetate, propionate, butyrate, isobutyrate, isovalerate, isocaproic acid, hexanoic acid, and heptanoic acid were below detection in all of the tested oil samples including the MB 12-35 oil. Propionic acid was detected at a relatively low concentration (0.28 mM) in the Nine Mile 10-7 oil sample. This argued for either microbial or abiotic generation of acetate in the autoclaved controls.

Formation water in both the MBP-01 MB 12-35 sterile and MBP-01 MB 12-35 hydrogen+Minerals+Metals+Vitamins+YE samples were turbid in appearance and contained numerous microbial cells visualized with the microscope. Significantly higher numbers of microorganisms were observed in the non-autoclaved sample. This suggested that the sterile controls were not sterile at the time the liquid samples were collected for microscopic examination. The finding that acetate but not methane is produced in the sterile controls argues that cross contamination from live to sterile incubations during sampling (via sterile syringes and needles) is not the source of microorganisms in the sterile controls. Cross contamination would also have transferred methanogens resulting in methanogenesis. These results argue for a microbial source of acetate production in these autoclaved incubations although more definitive analyses were conducted for confirmation.

Figure 5:
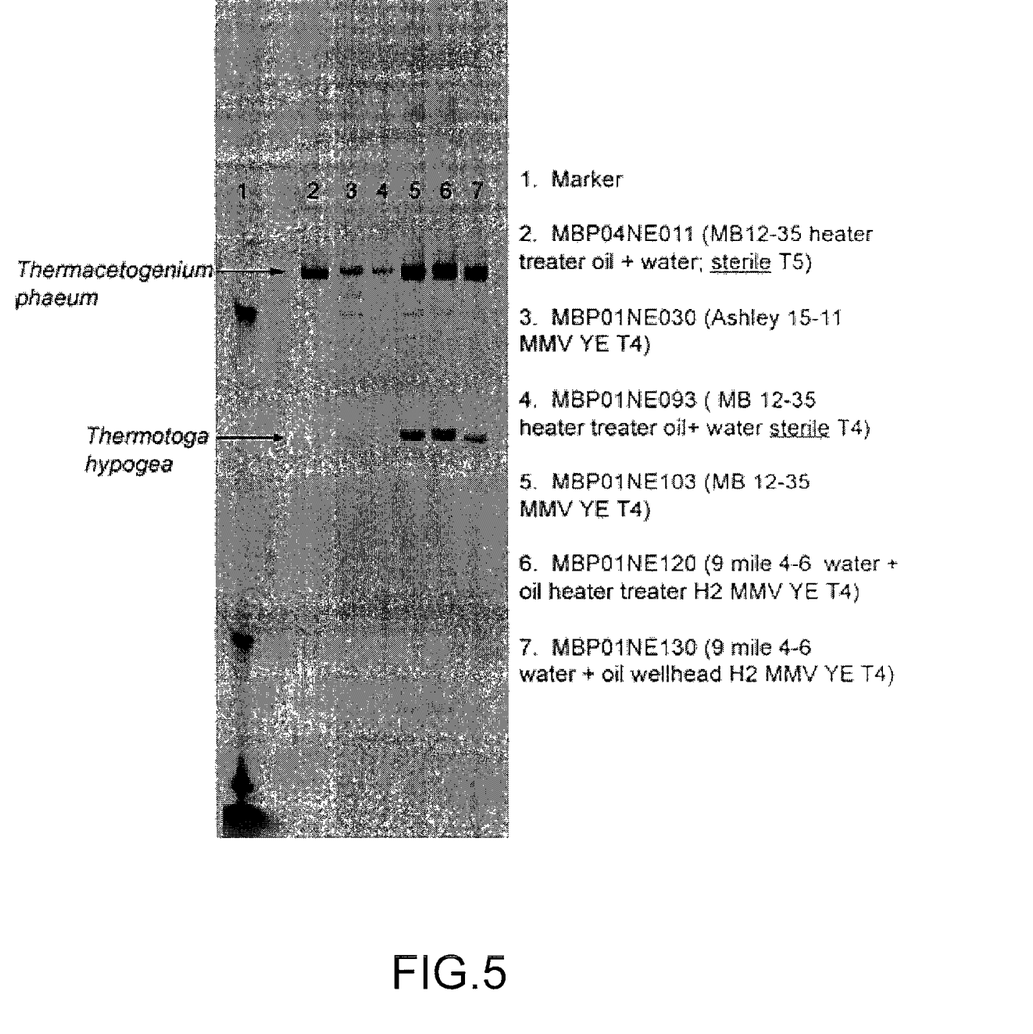
FIG. 5 is a TRFLP banding pattern of DNA samples taken from consortium microorganisms.

Experimental bottles, including MBP01, NE093 and MBP04NE011, all of which are autoclaved incubations that generated significant acetate, were sampled and analyzed to identify the identity of microorganisms within the aqueous phase. FIG. 5 shows the TRFLP banding patterns for the DNA obtained from several MBP-01 incubations.

*Thermacetogenium phaeum* was the only microorganism detected in the MB12-35 autoclaved incubations analyzed from independent experiments. In contrast, four different microorganisms, including *Thermotoga hypogea* were present in live (non-autoclaved) incubations prepared with the MB12-35 production fluid and oil. These results conclusively indicate that *Thermacetogenium phaeum* (or *T. phaeum* spores) survived three cycles of autoclaving and that *Thermacetogenium phaeum* is capable of producing acetate from hydrocarbons contained within the samples.

Figure 6A:
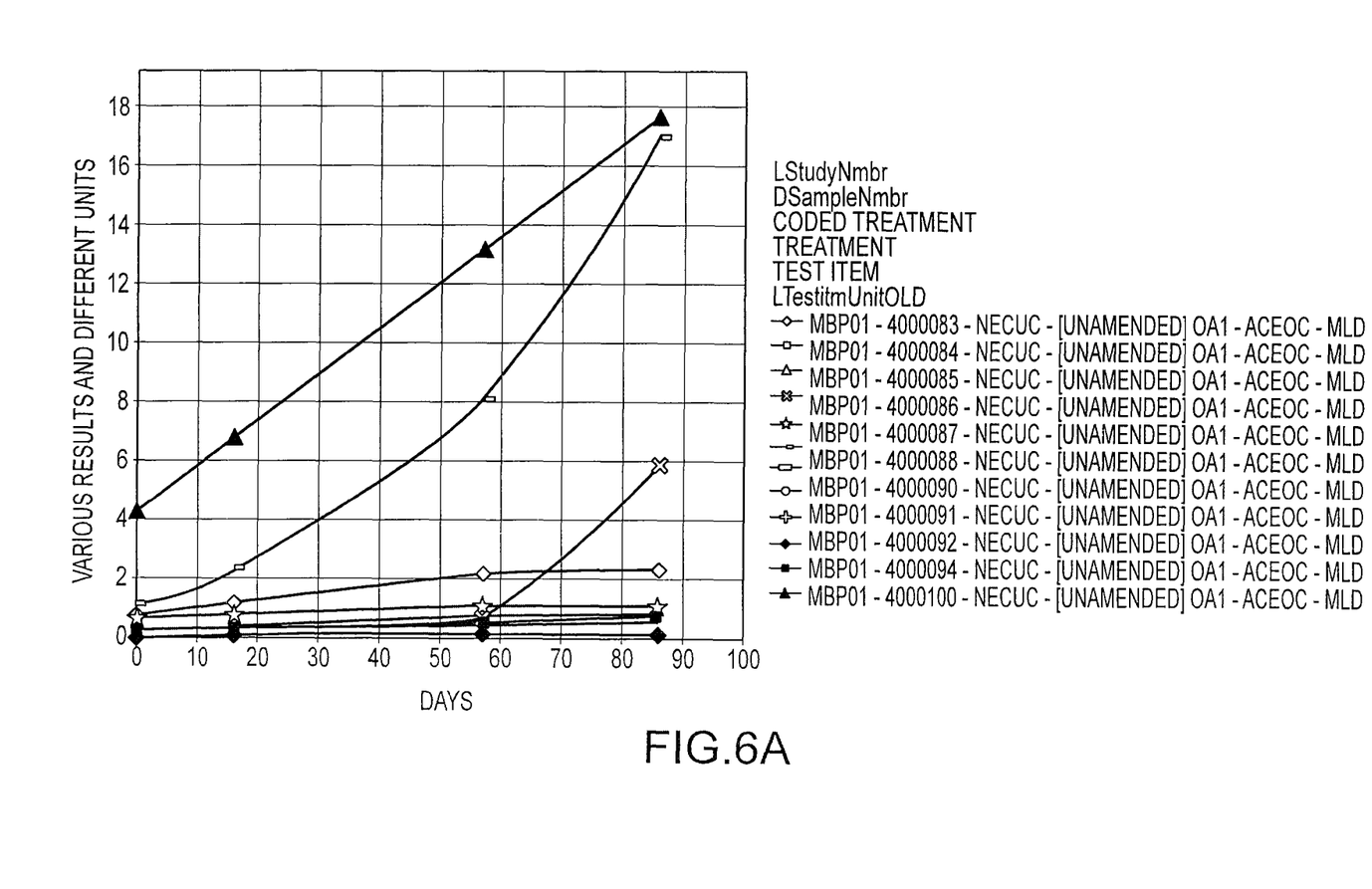
FIG. 6A is a graph of acetate concentrations in autoclaved formation water.
Figure 6B:
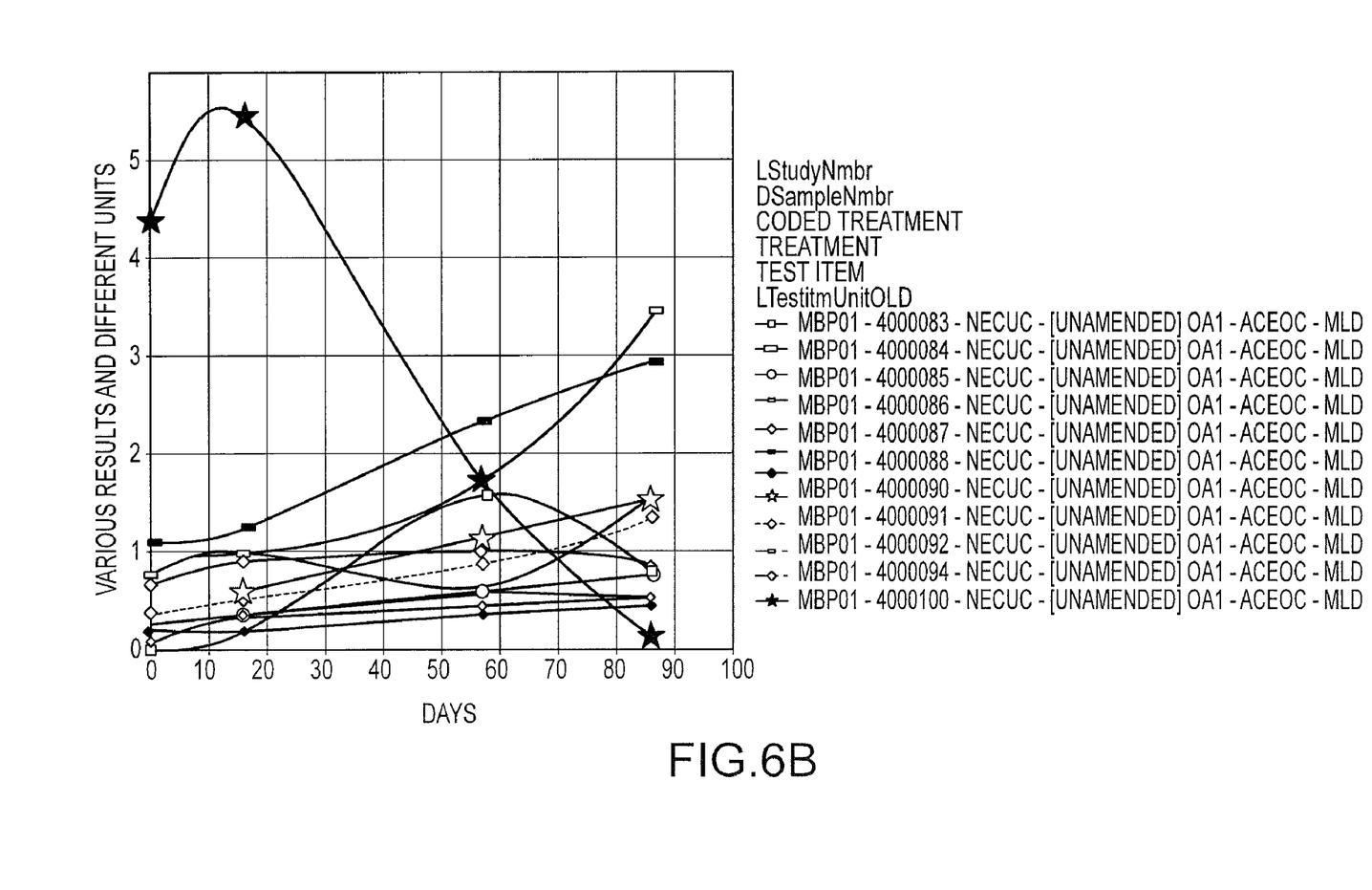
FIG. 6B is a graph of acetate concentrations in unamended incubations.

Acetate production was determined in several autoclaved Monument Butte incubations to further evaluate the significance of the findings with the MB 12-35 sample. FIGS. 6A-B plot the concentration of acetate in autoclaved control samples (FIG. 6A) and unamended, unautoclaved incubations (FIG. 6B). Very significant acetate production was observed in three of the autoclaved samples and at least some acetate accumulated in most of the autoclaved samples. In five of twelve samples, acetate accumulated to a greater extent and at faster rates in autoclaved controls, relative to unamended incubations. Interestingly, included within the group of samples that generated high acetate in sterile controls were all three samples that generated methane to a significantly higher extent (>18.5% headspace methane) in the corresponding unamended controls.

Based on the these results, *Thermacetogenium phaeum* was identified as the first bite species that metabolized the starting complex hydrocarbon substrate (crude oil) into acetate. *Thermacetogenium phaeum* is a homoacetogenic bacterium that can grow on various substrates, such as methoxylated aromatics, pyruvate, glycine, cysteine, formate and hydrogen/$CO_2$. *T. phaeum* is a gram-positive, spore-forming, and rod-shaped microorganism growing optimally at 58° C. and pH 6.8. It can also grow on acetate if cocultured with a hydrogen-consuming methanogenic partner, such as *Methanothermobacter thermautotrophicus*.

Having described several embodiments, it will be recognized by those of skill in the art that various modifications, alternative constructions, and equivalents may be used without departing from the spirit of the invention. Additionally, a number of well known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the electrode" includes reference to one or more electrodes and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A method of increasing production of materials with enhanced hydrogen content, the method comprising:
    isolating *Thermacetogenium phaeum* from geologic formation water;
    culturing the isolated *Thermacetogenium phaeum* to increase the *Thermacetogenium phaeum* population; and
    introducing a consortium comprising the cultured *Thermacetogenium phaeum* into a hydrocarbon formation containing a complex hydrocarbon substrate.

2. The method of claim 1, wherein the method comprises causing at least a portion of the cultured *Thermacetogenium phaeum* to sporulate.

3. The method of claim 2, wherein the *Thermacetogenium phaeum* sporulates by heating the *Thermacetogenium phaeum* to a temperature of about 120° C.

4. The method of claim 1, wherein the *Thermacetogenium phaeum* sporulates by dehydrating the *Thermacetogenium phaeum*.

5. The method of claim 1, wherein the method comprises germinating the spores of the cultured *Thermacetogenium phaeum* that were introduced to the hydrocarbon formation.

6. The method of claim 1, wherein the geologic formation water is taken from the hydrocarbon formation.

7. The method of claim 1, wherein isolating the *Thermacetogenium phaeum* comprises autoclaving the formation water.

8. The method of claim 7, wherein the formation water is autoclaved at about 120° C. for about 20 minutes at about 15 psi.

9. The method of claim 8, wherein the formation water is autoclaved in at least three successive cycles.

10. The method of claim 1, wherein the isolated *Thermacetogenium phaeum* is cultured in an environment comprising a growth stimulant.

11. The method of claim 10, wherein the growth stimulant is selected from the group consisting of sodium pyruvate.

12. The method of claim 1, wherein the hydrocarbon formation comprises a mature oil field.

13. The method of claim 1, wherein the complex hydrocarbon substrate is selected from the group consisting of oil, oil shale, tar sands, and tar.

14. The method of claim 1, wherein the complex hydrocarbon substrate is selected from the group consisting of coal, lignite, peat, or carbonaceous shale.

* * * * *